United States Patent [19]
Wilkins

[11] Patent Number: 6,136,299
[45] Date of Patent: Oct. 24, 2000

[54] SUNSCREEN COMPOSITION AND METHOD OF PRODUCING SAME

[75] Inventor: Brian Joseph Wilkins, Wellington, New Zealand

[73] Assignee: Donville Holdings Limited, Wellington, New Zealand

[21] Appl. No.: 09/380,635

[22] PCT Filed: Mar. 6, 1998

[86] PCT No.: PCT/NZ98/00029

§ 371 Date: Mar. 9, 1999

§ 102(e) Date: Sep. 3, 1999

[87] PCT Pub. No.: WO98/38965

PCT Pub. Date: Sep. 11, 1998

[30] Foreign Application Priority Data

Mar. 7, 1997 [NZ] New Zealand ............................ 314361
Dec. 19, 1997 [NZ] New Zealand ............................ 329381

[51] Int. Cl.[7] ................................ A61K 7/42; A61K 7/44; A61K 7/00
[52] U.S. Cl. ............................... 424/59; 424/60; 424/400; 424/401
[58] Field of Search ................................ 424/59, 60, 400, 424/401

[56] References Cited

FOREIGN PATENT DOCUMENTS 9311135  6/1993  WIPO .

*Primary Examiner*—Shelley A. Dodson
*Attorney, Agent, or Firm*—Reed Smith Shaw & McClay LLP

[57] ABSTRACT

This invention relates to a composition suitable for application to the skin of a human for use as a sunscreen product, the composition having been formed by combining a metal carboxylate, a medium, and an ultra-violet radiation absorbing agent, the metal carboxylate and the medium together forming a viscous gel or fluid containing the absorbing agent. The invention further includes a method of producing a sunscreen product comprising the steps of combining the ingredients above and heating the mixture to a sufficient temperature and for a sufficient period of time to dissolve the metal carboxylate, and suitably cooling the mixture to produce a gel sunscreen product.

20 Claims, No Drawings

SUNSCREEN COMPOSITION AND METHOD OF PRODUCING SAME

TECHNICAL FIELD

This invention relates to sunscreen compositions.

BACKGROUND OF THE INVENTION

Many modern sunscreens are formulated to achieve high sun protection factors (SPF). It is desirable that such sunscreens be able to remain on the skin for long periods of time, even during or after immersion in water, or in the presence of perspiration. The ability of a sunscreen to remain on the skin is referred to herein as its substantivity.

For convenience of manufacture, and to achieve desirable cosmetic properties such as ease of spreading, most sunscreen compositions are formulated as emulsions comprising an oil phase and a water phase. A disadvantage of emulsions is that they may involve the use of hydrophilic surfactants, and these can significantly reduce the substantivity of the associated sunscreen.

It is an object of at least one form of the present invention to provide a sunscreen composition that has substantial substantivity.

BRIEF DESCRIPTION OF THE INVENTION

According to one aspect of the invention there is provided a composition suitable for application to the skin of a human for use as a sunscreen. the composition having been formed by combining the following ingredients:

a) a metal carboxylate,
b) a medium, and
c) an ultra-violet radiation absorbing agent, the metal carboxylate and the medium together forming a viscous gel or fluid containing the absorbing agent.

Preferably the metal carboxylate comprises a metal stearate, for example magnesium stearate, aluminium stearate, or aluminium monostearate.

Alternatively other metal carboxylates of similar long chain organic acids included branched or unbranched saturated or unsaturated acids can be used.

Conveniently the metal carboxylate makes up approximately 12% to approximately 20% by weight of the ingredients.

Desirably the medium comprises approximately 20% to approximately 30% by weight of a volatile silicone, for example cyclomethicone.

Expediently the medium comprises approximately 2% to approximately 5% by weight of a non-volatile silicone, for example phenyldimethicone.

Optionally the ultra-violet radiation absorbing agent comprises all or some of the following substances:

a) 2-ethylhexyl paramethoxycinnamate, preferably in the amount of approximately 7% to approximately 10% by weight,
b) 1-(4 tert-butylphenyl)-3-(4-methoxyphenyl) propane-1-3-dione (also known as butylmethoxydibenzoyl methane) preferably in the amount of approximately 1% by weight,
c) octyl triazone, preferably in the amount of approximately 2% to approximately 5% by weight,
d) octyl salicylate, preferable in the amount of approximately 2% to approximately 5% by weight, and
e) titanium dioxide, preferably in the amount of approximately 2% to approximately 5% by weight.

Advantageously the ingredients comprise isopropyl myristate, preferably in the amount of approximately 10% to approximately 26% by weight.

According to a further aspect of the invention there is provided a method of producing a sunscreen composition comprising the steps of:

(i) combining the metal carboxylate, the medium, and the ultra-violet radiation absorbing agent to form a mixture thereof,
(ii) heating the mixture to a sufficient temperature and for a sufficient period of time to dissolve the metal carboxylate, and
(iii) suitably cooling the mixture, preferably by agitation, to produce a gel sunscreen composition.

Desirably the mixture is agitated during the heating of step (ii).

Conveniently during step (ii) the mixture is held at a temperature of approximately 120 degrees Celsius, preferably for approximately 10 minutes.

Expediently the cooling at step (iii) is at a rate of approximately 20 degrees Celsius per minute, preferably for approximately 4–5 minutes.

DETAILED DESCRIPTION OF THE PREFERRED EMBODIMENT

Some aspects of the invention will now be described by way of example, although it should be appreciated that the invention is in no way limited to such examples.

It has been surprisingly found that in the production of sunscreen compositions a pharmaceutically acceptable metal carboxylate, such as magnesium stearate, is effective both as a gelling agent and as a water repellent.

A preferred sunscreen composition according to the invention generally excludes components of a distinct hydrophilic nature, for example water hydrophilic surfactants and hydrophilic excipients. The avoidance of water hydrophilic surfactants and hydrophilic excipients enables the composition, which is in the form of a gel, to display significant substantivity. The sunscreen composition is designed to provide a high degree of protection in the UVA and UVB regions, with an SPF of between approximately 20 to 50. It will be appreciated that the percentage by weight of ultra-violet radiation or light absorbing agents in the composition will affect the SPF value.

EXAMPLE A

After many trials, the following ingredients were chosen as a sunscreen composition that resulted in an advantageous product.

| Ingredients | Percent by weight |
| --- | --- |
| 2-Ethylhexyl Paramethoxycinnamate | 10 |
| Octyl Triazone | 5.2 |
| Octyl Salicylate | 5.2 |
| Butylmethoxydibenzoyl methane | 1.1 |
| Tioveil IPM | 6 |
| Cyclomethicone | 30 |
| Phenyldimethicone | 5 |
| Tocopheryl Acetate | 0.5 |
| Acetulan (grade of acetylated lanolin) | 5 |
| Magnesium Stearate | 18.9 |
| Isopropyl Myristate | 13.1 |

The gel product resulting from this composition, after being produced by the previously mentioned method, was found to offer many desirable features. For example, the product was found to have a smooth consistency, was easy to apply to the skin, had a pleasant aroma, and was relatively grease free to the touch. Moreover, the product was non-irritating and non-toxic. The composition was found to be cosmetically acceptable, remaining visibly transparent upon the skin whilst still being capable of absorbing substantial UV radiation. A further desirable feature was that it was found to be stable over a period of time, both under temperature fluctuations and during storage at 40 degrees Celsius.

A sample of product made according to Example A was tested for substantivity and effectiveness. The test results carried out according to the joint Australia/New Zealand Standard 2604:1997 for sunscreen products indicated the product did not transmit more than 10% of ultraviolet radiation at any wavelength between 320 nm and 360 nm. Furthermore, after the product was tested on the skin of human subjects according to the standard 2604:1997 at the Australian Photobiology testing facility at the University of Sydney, it was found to have a static SPF of 50.1, and after 4 hours of water immersion an SPF of 31.96.

This test indicated a high SPF factor having a long efficacy period, particularly after immersion in water. The excellent showing in the immersion test indicated that the product should provide good sun protection in the presence of perspiration during normal activity or sport.

The magnesium stearate was found to be an excellent gelling agent, and offered the additional advantage of enhancing the water repellency of the composition.

The ultra-violet radiation absorbers in the sunscreen product include 2-ethylhexyl paramethoxycinnamate, butyl-methoxydibenzoyl methane, octyl salicylate, octyl triazone, and finely divided titanium dioxide. The test showed that they provided sunscreen protection across both the UVA and UVB regions Butylmethoxydibenzoyl methane increased the stability of the product. It also softened the gel and gave rise to a smooth product by preventing the gel from becoming too granular in texture.

Octyl salicylate was found to increase the solubility of the magnesium stearate, and improved the gel appearance by softening the gel.

Octyl triazone was found to be compatible with the other ingredients.

Cyclomethicone and phenyldimethicone served to allow the magnesium stearate to dissolve at a lower temperature when heated, and functioned as a hydrophobic vehicle in the composition. They had the effect of softening the gel product. Cyclomethicone facilitated easy spreading when the product was applied to the skin, and was found not to be too oily.

Isopropyl myristate is an oil soluble emollient. Acetulan was found to improve the texture of the product, to assist in preventing stiffness in the product, and to discourage the formation of lumps.

Tioveil aids in binding the gel into a stable structure, and enhances the overall stability of the product.

Tocopheryl acetate is an antioxidant enhancing the stability of the product when exposed to air and radiation, as well as conferring a possible benefit as a scavenger of harmful free radicals formed when UV radiation penetrates the skin.

EXAMPLE B

A trial was conducted with a sunscreen composition according to an aspect of the invention in combination with an insect repellent compound. The trialled product was formulated as follows:

| Ingredients | Percent by weight |
| --- | --- |
| 2-Ethylhexyl Paramethoxycinnamate | 7.5 |
| Octyl Salicylate | 8.5 |
| Butylmethoxydibenzoyl methane | 1.1 |
| Tioveil IPM | 11 |
| Cyclomethicone | 28.9 |
| Phenyldimethicone | 5 |
| Tocopheryl Acetate | 0.5 |
| Acetulan | 5 |
| Magnesium Stearate | 15.5 |
| Titanium Dioxide | 12 |
| Citronella Oil | 5 |

The resulting product was found to be effective as an insect repellent. The gel product was stable and of good consistency.

EXAMPLE C

An alternative sunscreen composition using aluminium monostearate includes the following ingredients:

| Ingredients | Percent by weight |
| --- | --- |
| 2-Ethylhexyl Paramethoxycinnamate | 10 |
| Octyl Salicylate | 5.2 |
| Butylmethoxydibenzoyl methane | 1.1 |
| Tioveil IPM | 6 |
| Cyclomethicone | 30 |
| Phenyldimethicone | 5 |
| Tocopheryl Acetate | 0.5 |
| Acetulan (grade of acetylated lanolin) | 5 |
| Aluminium monostearate | 12 |
| Isopropyl Myristate | 25.2 |

EXAMPLE D

A simple barrier gel was devised as follows:

| Ingredients | Percent by weight |
| --- | --- |
| Isopropyl myristate | 85 |
| Magnesium Stearate | 15 |

The product was stable.

The sunscreen compositions according to the invention can be produced using a variety of ingredients in a range of percentages by weight. The mix of ingredients settled on in each case will depend on the desired hydrophobicity, and on the desired SPF value. Preferably the sunscreen comprises approximately 1% to approximately 30% by weight of ultra-violet radiation absorbing (ie. blocking) agent.

The above Examples were formed by way of a particular method of production as will now be discussed. The method involves combining the ingredients to form a mixture, and then agitating and heating the mixture to a sufficient temperature, preferably not less than 105 degrees Celsius, to dissolve the metal carboxylate. After the carboxylate is dissolved the mixture is then cooled and agitated at an appropriate rate of cooling to produce a gelled sunscreen composition. The cooling rate is preferably above 15 degrees Celsius per minute, and more desirably approximately 20 degrees Celsius per minute, for approximately 4 to 5 minutes until the product gels as desired. The temperature of the cooled gel is preferably between approximately 15 and approximately 45 degrees Celsius depending on the ingredients of the mixture and the result desired. The apparatus used for cooling the mixture must accomplish this without creating instability in the gel structure through unnecessarily violent agitation.

The apparatus for cooling the mixture comprises a vessel, which is surrounded by a jacket through which cooling water is pumped. Desirably the apparatus has scrapers or paddles which scrape the inner surface of the vessel and move the mixture during cooling and formation of gel on cold walls of the vessel. Shearing is greatly reduced during cooling of the mixture because the pushing action of the paddles is not violent.

Additional advantages of the present invention will become apparent for those skilled in the art after considering the principles in particular form as discussed and illustrated. Thus, it will be understood that the invention is not limited to the particular embodiments described and exemplified, but is intended to cover all alterations or modifications which are within the scope of the appended claims.

What is claimed is:

1. The composition suitable for application to the skin of a human for use as a sunscreen, the composition having been formed by combining the following ingredients:
    a) a metal carboxylate,
    b) a medium, and
    c) an ultra-violet radiation absorbing agent,
the metal carboxylate and the medium together forming a viscous gel or fluid containing the absorbing agent, the composition excluding emulsifying agents.

2. The composition according to claim 1, wherein the metal carboxylate comprises a metal stearate.

3. The composition according to claim 1, wherein the metal carboxylate comprises magnesium stearate, aluminum stearate, or aluminum monostearate.

4. The composition according to claim 2, wherein the metal carboxylate makes up approximately 12% to approximately 20% by weight of the ingredients.

5. The composition according to claim 1, wherein the medium causes the composition to be substantially hydrophobic.

6. The composition according to claim 1, wherein the medium comprises a volatile silicone.

7. The composition according to claim 1, wherein the medium comprises a non-volatile silicone.

8. The composition according to claim 1, wherein the ultra-violet radiation absorbing agent comprises one or more of the following substances:
    a) 2-ethylhexyl paramethoxycinnamate,
    b) 1-(4 tert-butylphenyl)-3-(4-methoxyphenyl) propane-1-3-dione,
    c) octyl triazone,
    d) octyl salicylate, and
    e) titanium dioxide.

9. The composition according to claim 1, comprising isopropyl myristate.

10. The composition according to claim 1, wherein the ingredients comprise at least one of the following substances:
    a) approximately 12% to approximately 20% by weight magnesium stearate,
    b) approximately 20% to approximately 30% by weight volatile silicone,
    c) approximately 2% to approximately 5% by weight non-volatile silicone, and
    d) approximately 1% to approximately 30% by weight ultra-violet radiation absorbing agent.

11. The composition according to claim 1, wherein the ultra-violet radiation absorbing agent comprises at least one of the following substances:
    a) approximately 7% to approximately 10% by weight 2-ethylhexyl paramethoxycinnamate,
    b) approximately 1% by weight butylmethoxydibenzoyl methane,
    c) approximately 2% to approximately 5% by weight octyl salicylate, and
    d) approximately 2% to approximately 4% by weight titanium dioxide.

12. The composition according to claim 1, comprising approximately 10% to approximately 26% by weight isopropyl myristate.

13. The method of producing a sunscreen composition according to claim 1, comprising the steps of:
    (i) combining the ingredients "a", "b" and "c" as set out in claim 1 to form a mixture thereof
    (ii) heating the mixture to a sufficient temperature and for a sufficient period of time to dissolve the metal carboxylate, and
    (iii) suitably cooling the mixture to produce a gel sunscreen composition.

14. The method according to claim 13, wherein the mixture is agitated during the heating of step (ii).

15. The method according to either claim 13, wherein during step (ii) the mixture is held at a temperature of approximately 120 degrees Celsius.

16. The method according to either claim 14, wherein during step (ii) the mixture is held at a temperature of approximately 120 degrees Celsius.

17. The method according to claim 13, wherein during step (ii) the mixture is held at a temperature of approximately 120 degrees for approximately 10 minutes.

18. The method according to claim 13, wherein the cooling at step (iii) is at a rate of approximately 20 degrees Celsius per minute.

19. The method according to claim 13, wherein the cooling at step (iii) is at a rate of approximately 20 degrees Celsius per minute for approximately 4 to approximately 5 minutes.

20. The sunscreen composition formed according to the method of claim 13.

* * * * *